US012767621B2

(12) United States Patent
Schuetzle et al.

(10) Patent No.: US 12,767,621 B2
(45) Date of Patent: Oct. 20, 2026

(54) PROCESS AND CATALYSTS FOR THE PRODUCTION OF ETHYLENE AND PROPYLENE FROM LOW-CARBON SYNGAS

(71) Applicant: Greyrock Technology, LLC, Sacramento, CA (US)

(72) Inventors: Robert Schuetzle, Sacramento, CA (US); Dennis Schuetzle, Grass Valley, CA (US)

(73) Assignee: Greyrock Technology, LLC, Sacramento, CA (US)

( * ) Notice: Subject to any disclaimer, the term of this patent is extended or adjusted under 35 U.S.C. 154(b) by 92 days.

(21) Appl. No.: 18/445,319

(22) Filed: Jul. 7, 2023

(65) Prior Publication Data

US 2025/0011259 A1 Jan. 9, 2025

(51) Int. Cl.

| | |
|---|---|
| ***C07C 1/04*** | (2006.01) |
| ***B01J 21/00*** | (2006.01) |
| ***B01J 23/00*** | (2006.01) |
| ***B01J 23/06*** | (2006.01) |
| ***C07C 11/04*** | (2006.01) |
| ***C07C 11/06*** | (2006.01) |

(52) U.S. Cl.

CPC ............. *C07C 11/06* (2013.01); *B01J 21/005* (2013.01); *B01J 23/005* (2013.01); *B01J 23/06* (2013.01); *C07C 1/04* (2013.01); *C07C 11/04* (2013.01)

(58) Field of Classification Search

CPC ........... C07C 11/04; C07C 11/06; C07C 1/04; C07C 1/043; C07C 2523/06; B01J 23/005; B01J 23/06; B01J 21/005; B01J 35/40; B01J 35/613; Y02P 20/52

See application file for complete search history.

(56) References Cited

U.S. PATENT DOCUMENTS 10,960,387 B2 * 3/2021 Bao ........................ C07C 1/0455

FOREIGN PATENT DOCUMENTS

CN 112705258 A * 4/2021

OTHER PUBLICATIONS

Fu et al. "Enhancing syngas-to-aromatics performance of ZnO&H—ZSM-5 composite catalyst via Mn modulation" Journal of Catalysis, 2020, 97-102, 383.

Torres Galvis et al. "Catalysts for production of lower olefins from synthesis gas: a review", ACS Catal., 2013, 2130-2149, 3.

Gao et al. "Recent advances in intensified ethylene production—a review", ACS Catal., 2019, 8592-8621, 9.

Gibb et al. "Lung cancer among workers in chromium chemical production", American Journal of Industrial Medicine, 2000, 115-126, 38.

Jiao et al. "Selective conversion of syngas to light olefins", Science, (2016, 1065-1068, 351.

Liu et al. "Design of efficient bifunctional catalysts for direct conversion of syngas into lower olefins via methanol/dimethyl ether intermediates", Chem Sci., 2018, 4708-4718, 9.

Mao et al. "Efficient syngas-to-olefins conversion via Kaolin Modified SAPO-34 catalyst", Catalysis Letters, 2024, 664-673, 154.

Su et al. "High conversion of syngas to ethene and propene on bifunctional catalysts via the tailoring of SAPO zeolite structure", Cell Reports Physical Science, 2021, 1-13, 2.

Tihay et al. "Effect of Fischer-Tropsch synthesis on the microstructure of Fe—Co-based metal/spinel composite materials", Applied Catalysis A: General, 2001, 29-42, 206.

Yu et al. "Direct production of olefins from syngas with ultrahigh carbon efficiency", Nature Communications, 2022, 5987-5997, 13.

Zhai et al. "Highly tunable selectivity for syngas-derived alkenes over zinc and sodium-modulated Fe5C2 catalyst", Angew. Chem. Int. Ed., 2016, 9902-9907, 55.

Zhong et al. "Cobalt carbide nanoprisms for direct production of lower olefins from syngas", Nature. 2016, 84-87, 538.

Matveyeva et al. "Catalyst supports based on Zn—O—ZnAl2O4 nano-composites with enhanced selectivity and coking resistance in isobutane dehydrogenation", Dalton Trans. 2022, 12213-12224, 51.

* cited by examiner

*Primary Examiner* — Youngsul Jeong
*Assistant Examiner* — Jason Y Chong
(74) *Attorney, Agent, or Firm* — McKinney Law Group APC; Jeffrey A. McKinney

(57) ABSTRACT

An improved process and catalysts for efficiently producing ethylene and propylene from low-carbon syngas is described. The process comprises contacting the low-carbon syngas with a ZnO-impregnated $ZnMoO_4$ spinel catalyst or a ZnO-impregnated $ZnAl_2O_4$ spinel catalyst; wherein the said catalysts demonstrate selectivities of up to about 80% for C2-C4 alkenes, at syngas $H_2$/CO ratios of 1.0 to 3.0, at temperatures of 250 to 425° C. (482-797° F.), at pressures of 150 to 350 psi, and at space velocities of 4,000 to 15,000 $hr^{-1}$ with CO conversion efficiencies of 40-55%.

9 Claims, No Drawings

PROCESS AND CATALYSTS FOR THE PRODUCTION OF ETHYLENE AND PROPYLENE FROM LOW-CARBON SYNGAS

FIELD OF THE INVENTION

A process and catalysts for efficiently producing ethylene and propylene from low-carbon syngas.

BACKGROUND OF THE INVENTION

Plastics have undoubtedly revolutionized numerous industries, providing countless benefits and conveniences. However, the production of plastics comes at a significant environmental cost, particularly in relation to carbon emissions.

Crackers play a crucial role in the conventional production of plastics. They are responsible for breaking down hydrocarbon molecules derived primarily from fossil fuels, such as crude oil and natural gas. The cracking process releases ethylene and propylene, which serve as the building blocks for the production of various plastic polymers.

While crackers are essential in meeting the ever-growing demand for plastics, they come with a significant carbon emissions footprint. The cracking process involves the release of substantial amounts of greenhouse gases, including carbon dioxide and methane, into the atmosphere. These emissions contribute to global warming, climate change, and other environmental concerns.

Multiple factors contribute to the generation of carbon emissions during the cracking process, including:

1. Energy Intensity: Crackers require vast amounts of energy, primarily in the form of fossil fuels, to break down the hydrocarbon molecules. This energy expenditure results in substantial carbon dioxide emissions.
2. Feedstock Composition: The type and quality of feedstock used in crackers can impact the carbon emissions. Fossil fuels with higher carbon content, such as heavier petroleum fractions, tend to release more carbon emissions during cracking.
3. Byproduct Emissions: The cracking process can produce unintended byproducts, including methane, a potent greenhouse gas. Methane emissions arise from leaks, flaring, or incomplete combustion of gases released during the cracking process.

The reliance on crackers for ethylene and propylene production poses significant challenges in mitigating carbon emissions within the plastics industry. Limiting or eliminating the use of crackers entirely is not feasible due to the essential role they play in plastics manufacturing. However, a paradigm shift is necessary to adopt more sustainable and eco-friendly alternatives.

There are many crackers that are operating today throughout the world. Some of the more well-known crackers in Europe and their locations include: Borealis Olefins Plant (Stenungsund, Sweden); INEOS Cracker Plant (Koln, Germany); LyondellBasell Cracker Plant (Maasvlakte, Netherlands); SABIC Cracker Plant (Gelsenkirchen, Germany); Shell Cracker Plant (Moerdijk, Netherlands); Total Cracker Plant (Antwerp, Belgium); Versalis Cracker Plant (Ferrara, Italy); Yara Cracker Plant (Sluiskil, Netherlands); Polimery Police Ethylene and Propylene Plant (Police, Poland); Borealis Ethylene and Propylene Plant (Stenungsund, Sweden).

Some of the more well-known crackers in the United States and their locations include: Chevron Phillips Chemical Company—Cedar Bayou Plant (Texas); ExxonMobil Chemical Company—Baytown Plant (Texas); Dow Chemical Company—Freeport Plant (Texas); Shell Chemical LP—Deer Park Plant (Texas); LyondellBasell Industries—La Porte Plant (Texas); Formosa Plastics Corporation—Point Comfort Plant (Texas); INEOS Olefins & Polymers USA—Chocolate Bayou Plant (Texas); Occidental Chemical Corporation—Ingleside Plant (Texas); Chevron Phillips Chemical Company—Sweeny Plant (Texas); ExxonMobil Chemical Company—Baton Rouge Plant (Louisiana).

Some of the more well-known crackers in Asia and, the Middle East and their locations include: Qatofin Olefins Plant (Qatar); Borouge Olefins Plant (UAE); Sadara Olefins Plant (Saudi Arabia); Jamnagar Olefins Plant (India); S-Oil Onsan Olefins Plant (South Korea); Formosa Petrochemical Olefins Plant (Taiwan); JGC Olefins Plant (Japan); Zhejiang Petrochemical Olefins Plant (China); Thai Olefins Plant (Thailand); Petronas Melaka Olefins Plant (Malaysia).

The most recent advancement in the conversion of syngas to olefins was reported by Mao, et al. (2023). They studied $Al_2Si_2O_5(OH)_4$ modified SAPO-34 molecular sieves for the production of C2-C4 olefins. They found that this catalyst converted CO with an efficiency of 506/o to C2-C4 olefins with a selectivity of 24%, and a $CO_2$ selectivity of 17%, at an $H_2$/CO ratio of 2.0, a temperature of 400° C., and a pressure of 450 psi. This 24% olefin selectivity is much lower than the 80% olefin selectivity achieved by the improved catalyst described herein. In addition, the 17% $CO_2$ selectivity is not commercially viable.

Yu et al (2022) tested a sodium (Na) promoted ruthenium (Ru) catalyst on $SiO_2$ for the conversion of syngas to C2-C5 olefins. Their catalyst had a Ru concentration of 5% and a Ru/Na ratio of 2.0. This catalyst was tested at 260° C., at a space velocity of 3,000 ml/g/hr, at 150 psi, and a $H_2$/CO ratio of 2.0/1.0 produced C2-C4 olefins with a selectivity of about 80%, a paraffin selectivity of 15%, a $CO_2$ selectivity of 2%, and a $CH_4$ selectivity of 3%. The productivity of the catalyst declined by 2-3% after about 500 hrs. on-line. Although the performance of this catalyst was better than other catalysts described in the current art, the requirement for significant amounts of Ru in the catalyst and the loss in catalyst productivity of 2-3% after about 500 hrs. is not commercially practical.

Su et al. (2021) and Jia et al. (2016) describe zinc chromate ($ZnCr_2O_4$) catalysts on zeolite substrates. Su found that this catalyst converts syngas ($H_2$/CO=1.0) with a CO conversion efficiency of about 20% at 350-425° C. and a pressure of 150-350 psi with a selectivity of about 80% for C2-C4 olefins. Jia also reported a C2-C4 olefin selectivity as high as 80% at a CO conversion efficiency of about 20%. These CO conversion efficiencies are too low to be commercially feasible. In addition, zinc chromate contains hexavalent chromium which is classified as a human carcinogen (Gibb et al., 2000).

Lui et al (2018) described Zn impregnated on $ZrO_2$ nanoparticles and zeolite SSZ-13 nanocrystals. Although the selectivity of the C2-C4 olefins was 75% at $H_2$/CO of 2.0, 450 psi and 400° C., the $CO_2$ selectivity was high (25%) and the CO conversion per pass was only 23%.

Jiao et al (2016) reported the conversion of syngas to olefins using $ZnCrO_4$ impregnated on zeolite substrates. They reported a C2-C4 selectivity as high as 80% at a CO conversion of 17% but the single pass conversion was 17% which is too low to be commercially feasible.

Tihay et al (2001) reported on Co—Fe catalysts impregnated on spinel substrates. The highest C2-C4 olefin selectivity was observed for a catalyst with a Co/Fe ratio of 0.45.

This catalyst was tested at 250° C., 150 psi and an $H_2$/CO ratio of 1.0. It had a low CO conversion of about 5%, a C2-C4 olefin selectivity of 52% but with high methane production of 34%. This low CO conversion and high methane production demonstrates that this is not a commercially viable catalyst.

Several investigators have described the bimetallic alloy catalysts such as cobalt (Co) and iron (Fe) supported on silicon dioxide for the production of C2-C4 olefins with a selectivity of up to 70%. However, silicon dioxide can react with hydrogen in the syngas to produce silicon hydride resulting in the degradation of the catalyst with time.

Carbon-based catalysts are also gaining attention for olefin production from syngas. They are porous materials with high surface areas and good thermal stability. Graphene-based catalysts, for instance, have shown promising results in the production of olefins with a selectivity of up to 50%. However, graphene-based catalyst substrates don't have a high enough hardness for commercial applications.

Therefore, there is a need for the production of ethylene and propylene directly from alternative resources other than petroleum derived products and using an alternate process other than the use of "crackers" is needed.

SUMMARY OF THE INVENTION

This invention describes improved catalysts and processes for producing low-carbon ethylene and propylene from low-carbon syngas. The catalysts are comprised of ZnO impregnated on $ZnMoO_4$ or $ZnAl_2O_4$ spinels. These catalysts are synthesized by an improved process which blends micron-sized particles of ZnO with $Mo_2O_3$ or $Al_2O_3$, followed by pelletization and calcination up to 1,000° C. The resulting catalysts have a ZnO loading of about 0.10-25.0% by weight of the total catalyst. They have a selectivity of up to 80% for C2-C4 olefins at syngas $H_2$/CO ratios of 1.0-3.0, at temperatures of 250 to 425° C. (482-797° F.), at pressures of 100 to 350 psi, and at space velocities of 4,000 to 15,000 $hr^1$ with commercially feasible CO conversion efficiencies of 40-75%. The low-carbon ethylene and propylene are separated using distillation or adsorption. The low-carbon ethylene and propylene have carbon intensity values of less than 50% of traditional petroleum derived products.

DETAILED DESCRIPTION OF THE INVENTION

This invention relates to a production process for ethylene and propylene that involves the production of syngas from low carbon feedstocks and the direct conversion of the syngas into ethylene and propylene with high selectivity using a unique catalyst.

The process starts with the production of low carbon syngas, which is a mixture of hydrogen and carbon monoxide, that can be produced through various ways using low-carbon materials such as biomass, renewable natural gas, flare gas, $CO_2$ and $H_2$, municipal solid waste, or combinations thereof. Overall, there are many ways to produce syngas from low-carbon materials, and each method has its own advantages and challenges in terms of efficiency, cost, and environmental impact. Some of the methods used to produce syngas include:

Gasification: This process involves the conversion of solid or liquid feedstock, such as biomass or waste materials, into syngas. Gasification is usually done at high temperatures and in the presence of a controlled amount of oxygen, steam, or carbon dioxide. The feedstock is heated to high temperatures, and the resulting gases are cooled and cleaned to remove impurities such as ash and tar.

Pyrolysis: This is a process that involves the heating of organic materials in the absence of oxygen to produce syngas. The process can be used to convert biomass waste, such as sawdust and agricultural residues, into syngas.

Steam reforming: This process uses steam and a catalyst to convert biomass, natural gas, flare gas, or biomethane into syngas. This process is commonly used in commercial chemical production.

Carbon capture and utilization: This process involves the capture of $CO_2$ from industrial processes and using it to produce syngas through a process called reverse water-gas shift. This process involves the reaction of $CO_2$ and hydrogen (and/or steam) over a catalyst to produce syngas.

Biogas upgrading: Biogas produced from organic waste, such as food scraps and animal manure, can be upgraded to produce biomethane. Biomethane can then be converted to syngas through steam reforming or other traditional syngas production methods.

Flare gas utilization: Flare gas, which is a by-product of the oil and gas industry, can be used to produce syngas through a process called partial oxidation or steam reforming. This process involves the reaction of flare gas with oxygen and/or steam in a controlled environment.

The direct synthesis of $C_2$-$C_4$ alkenes from syngas has been a challenging area of research due to the complex reaction mechanism and the selectivity issues. Therefore, there is a need for an efficient catalyst that can convert syngas to C2-C4 alkenes with high selectivity.

Following the syngas production process, improved catalysts are used to convert the syngas to $C_2$-$C_4$ alkenes. The catalysts are comprised of 0.10 wt. % to 25 wt. % zinc oxide (ZnO) impregnated on a zinc molybdate ($ZnMoO_4$) or zinc aluminate ($ZnAl_2O_4$) spinel. The ZnO/$ZnMoO_4$ and ZnO/$ZnAl_2O_4$ catalysts have a surface area greater than 5 $m^2$/g, and adequate hardness for use in commercial-scale catalytic reactors.

These catalysts may be manufactured in several ways.

Impregnation of ZnO on $ZnMoO_4$ or $ZnAl_2O_4$. This process involves the preparation of the $ZnMoO_4$ spinel or $ZnAl_2O_4$ spinel followed by the impregnation of ZnO onto the spinels. The impregnated spinels are then calcined up to about 1,000° C.

The zinc oxide (ZnO) impregnated on zinc aluminate ($ZnAl_2O_4$) spinel is synthesized via a solid-state reaction of ZnO and $Al_2O_3$ (alumina) at temperatures up to about 1,000° C. (Equation 1) in which the molar ratios of ZnO to $Al_2O_3$ vary from 1.01-1.35 to produce a catalyst comprised of about 0.10 wt. % to 25 wt. % of ZnO impregnated on the $ZnAl_2O_4$ spinel.

$$ZnO + Al_2O_3 = Zn(Al_2O_4) + ZnO \qquad \text{Eq. 1}$$

The zinc oxide (ZnO) impregnated on zinc molybdate (ZnMoO4) spinel is synthesized via a solid-state reaction of state reaction of ZnO and $MoO_3$ (molybdenum oxide) at about 650° C. (Equation 2) in which the molar ratios of ZnO to $MoO_3$ vary from 1.01-1.75 to produce a catalyst comprised of about 0.10 wt. % to 25 wt. % of ZnO impregnated on the $ZnMoO_4$ spinel.

$$ZnO + MoO_3 = +Zn(MoO_4) + ZnO \qquad \text{Eq. 2}$$

Other methods such as co-precipitation, sol-gel, hydrothermal, and microwave-assisted synthesis may be employed for the synthesis of these catalysts. The choice of the manufacturing process is dependent upon the desired morphology, surface area, and stability of the catalyst.

The resulting ZnO impregnated spinel catalysts display a unique combination of properties, including high surface area, high stability, and high catalytic activity. These catalysts also demonstrate remarkable selectivity towards production of ethylene and propylene from syngas.

These catalysts convert syngas to $C_2$-$C_4$ alkenes with a selectivity of up to 80% (e.g., 30% to 80%, 40% to 80%, 50% to 80%, 60% to 80% and 70% to 80%) at syngas $H_2$/CO ratios of 1.0-2.2, at reactor temperatures of 250-425° C. (482-797° F.), at reactor pressures of 150-350 psi, and reactor space velocities of 4,000-15,000 $hr^{-1}$ with CO conversion efficiencies of 40-55%

The catalysts can be used in a fixed-bed reactor, a fluidized-bed reactor, or any other suitable reactor configuration. The syngas is fed to the reactor along with optionally a diluent gas such as nitrogen or argon. The reaction conditions are adjusted to optimize selectivities towards $C_2$-$C_4$ alkenes. Unreacted syngas is recycled back to the catalytic reactor.

These catalysts provide several advantages over the current state-of-the-art catalysts. Firstly, it exhibits a high selectivity towards $C_2$-$C_4$ alkenes, which are important building blocks for the synthesis of various plastic products and other chemicals. Secondly, it operates at relatively mild conditions of temperature and pressure, which reduces energy consumption and equipment costs. The spinel substrates are very stable and robust resulting in a catalyst that has a long lifetime without a loss in performance. The CO conversion efficiencies of 40-75% (e.g., 50-75%, 60-75%, 65-75%, 70-75%) are ideal for commercial scale catalytic reactors. In summary, this catalyst has several advantages over other catalysts described in the current art as described below.

REFERENCES

Fu, Y., Ni, Y., Zhu, W., Liu, Z.: Enhancing syngas to aromatics performance of ZnO and H-ZSM-5 composite via Mn Modulation. Journal of Catalysis, 383, 97-102 (2020). https://doi.org/10.1016/j.jcat.2019.12.044

Galvis, H. M. T., DeJong, K. P.: Catalysts for production of lower olefins from synthesis gas: a review. ACS Catalysis, 3, 2130-2149 (2013). https://doi.org/10.1021/cs4003436

Gao, Y., Neal, L., Ding, D., Wu, W., Baroi, C. H. Gaffney, A. M., Li, F.: Recent advances in Intensified Ethylene Production—A Review. ACS Catalysis, 9, 8592-8261 (2019). https://doi.org/10.1021/acscatal.9b02922

Gibb, H. J., Lees, P. S., Pinsky, P. F., Rooney, B. C.: Lung cancer among workers in chromium chemical production, American Journal of Industrial Medicine, 38.2, 115-126 (2000). https://doi.org/10.1002/1097-0274(200008)38:2

Jiao, F.; Li, J.; Pan, X.; Xiao, J.; Li, H.; Ma, H.; Wei, M.; Pan, Y.; Zhou, Z.; Li, M.: Selective conversion of syngas to light olefins. Science, 351, 1065-1068 (2016) https://doi.org/10.1126/science.aaf1835

Kim, H., Lee, S. K., Kim, K. H., Lee, J. S., & Bae, J. W.: Production of high-purity ethylene and propylene from syngas over Rh—Fe catalysts (2018)

Li, X., Li, J., Li, Y., Chen, J., Li, H., Wang, X., . . . & Liu, Y.: Co—Mn catalysts for selective syngas conversion to olefins: Effects of calcination temperature and Mn precursors. Catalysis Science & Technology, 9, 4189-4202 (2019).

Liu, Y., Syngas to ethylene and propylene over Co—Mo—Zn catalyst: Effect of operating parameters on product selectivity. Fuel, 216, 17-26 (2018).

Liu, X.; Zhou, W.; Yang, Y.; Cheng, K.; Kang, J.; Zhang, L.; Zhang, G.; Min, X.; Zhang, Q.; Wang, Y.: Design of efficient bifunctional catalysts for direct conversion of syngas into lower olefins via methanol/dimethyl ether intermediates. Chemical Science. 9, 4708-4718 (2018). https://doi.org/10.1039/C8SC01597J Mao, L., Zheng, H., Xiao, D., Ren, Y., Ran, L., Tang, J.: Efficient syngas to olefins conversion via kaolin modified SAPO-34 catalyst. Catalysis Letters (2023). https://doi.org/10.1007/s10562-023-04336-9

Su, J., Liu, C., Liu, S., Ye, Y., Du, Y., Zhou, H., Liu, S., Jiao, W., Zhang, L., Wang, C., Wang, Y., Xie, Z.: High Conversion of syngas to ethene and propene on bifunctional catalysts via the tailoring of SAPO zeolite structure. Cell Reports Physical Science, 2, 1 (2021).

Tihay, F., Pourroy, G., Richard-Plouet, M., Roger, A. C., Kiennemann, A.: Applied Catalysis A, 206, 29-42 (2001).

Yu, H., Wang, C., Lin, T., An, Y., Wang, Y., Chang, Q., Yu, F., Sun, F., Jiang, Z., Li, S., Sun, Y., Zhong, S.: Direct production of olefins from syngas with ultrahigh carbon efficiency, Nature Communications, 13, 5987 (2022). https://doi.org/10.1038/s41467-022-33715-w Zhai, P. et al.: Highly tunable selectivity for syngas-derived alkenes over zinc and sodium-modulated Fe—C catalyst. Angewandte Chem. International Edition, 55, 9902-9907 (2016). https://doi.org/10.1002/anie.201603556

Zhong, L. et al.: Cobalt carbide nanoprisms for direct production of lower olefins from syngas. Nature, 538, 84-87 (2016).

The invention claimed is:

1. A process for producing ethylene and propylene from syngas, wherein the process comprises: a conversion step consisting of contacting syngas with a catalyst at a syngas $H_2$/CO ratio ranging from 1.0 to 3.0, at a temperature ranging from 250° C. to 425° C., and at a pressure ranging from 100 psi to 350 psi, thereby producing ethylene and propylene from syngas in said conversion step, wherein the catalyst is a spinel, wherein the catalyst is either ZnO impregnated on $ZnMoO_4$ or ZnO impregnated on $ZnAl_2O_4$, and wherein the catalyst provides for a combined selectivity ranging from 50% to 80% for $C_2$-$C_4$ olefins and a CO conversion ranging from 40% to 75%.

2. The process of claim 1, wherein a loading percentage of the ZnO impregnated on $ZnMoO_4$ or $ZnAl_2O_4$ ranges from 0.10 weight percent to 25.0 weight percent.

3. The process of claim 1, wherein the conversion step further produces $CH_4$ at a $CH_4$ selectivity ranging from 0% to 5%.

4. The process of claim 1, wherein the ZnO is at least partially reduced to metallic zinc while in contact with the syngas.

5. The process of claim 1, wherein the produced ethylene and propylene are in a product stream, and wherein the process further comprises a separation step comprising separating the ethylene and propylene from one another by distillation or adsorption to provide purified ethylene and propylene.

6. The process of claim 1, wherein the syngas is produced by the gasification of agricultural waste or municipal solid waste.

7. The process of claim 1, wherein the syngas is produced by the gasification of biomass.

8. The process of claim 1, wherein the syngas is produced by the gasification of carbonaceous resources, and where the carbonaceous resources are flare gas, oil refinery waste, stranded gas, disadvantaged gas, used engine oil, waste tires, tar sands, oil shale, or combinations thereof.

9. The process of claim 1, wherein the syngas is produced by the catalytic conversion of captured $CO_2$ and renewable Hz.

* * * * *